(12) United States Patent
Benedetti et al.

(10) Patent No.: US 7,444,796 B2
(45) Date of Patent: Nov. 4, 2008

(54) METHOD AND PACKAGING MACHINE FOR PRODUCING SEALED PACKAGES OF POURABLE FOOD PRODUCTS FROM PRECUT BLANKS OF SHEET PACKAGING MATERIAL

(75) Inventors: Paolo Benedetti, Modena (IT); Alf Lindgren, Hjärup (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 10/512,585

(22) PCT Filed: Apr. 30, 2003

(86) PCT No.: PCT/EP03/04574

§ 371 (c)(1),
(2), (4) Date: May 20, 2005

(87) PCT Pub. No.: WO03/093113

PCT Pub. Date: Nov. 13, 2003

(65) Prior Publication Data

US 2005/0198924 A1    Sep. 15, 2005

(30) Foreign Application Priority Data

May 3, 2002  (IT)  .................... TO2002A0367

(51) Int. Cl.
*B65B 55/04* (2006.01)

(52) U.S. Cl. ............... 53/426; 53/167; 53/563; 141/92; 422/302

(58) Field of Classification Search .............. 53/426, 53/167, 456, 563; 141/92; 422/302, 307
See application file for complete search history.

(56) References Cited

U.S. PATENT DOCUMENTS

| | | | | |
|---|---|---|---|---|
| 3,566,575 A * | 3/1971 | Lisiecki | .................. | 53/426 |
| 3,929,952 A * | 12/1975 | Edwards | .................. | 264/521 |
| 3,954,375 A * | 5/1976 | Strzyzynski et al. | ........ | 425/403 |
| 4,566,251 A * | 1/1986 | Spisak et al. | .................. | 53/167 |
| 4,683,701 A * | 8/1987 | Rangwala et al. | .............. | 53/167 |
| 4,986,058 A * | 1/1991 | Carlsson et al. | ............... | 53/563 |
| 5,178,841 A * | 1/1993 | Vokins et al. | ............... | 422/298 |
| 5,587,127 A | 12/1996 | Carlson et al. | | |
| 5,879,648 A | 3/1999 | Kazuo et al. | | |
| 6,056,918 A * | 5/2000 | Palaniappan et al. | .......... | 422/24 |
| 6,066,081 A * | 5/2000 | Bachner | .................. | 493/102 |
| 6,622,457 B2* | 9/2003 | Kurth | .................. | 53/425 |
| 6,689,314 B2* | 2/2004 | Bushman et al. | .............. | 422/24 |

FOREIGN PATENT DOCUMENTS

| | | |
|---|---|---|
| EP | 0 481 361 A | 4/1992 |
| WO | WO 98 16259 A | 4/1998 |

\* cited by examiner

*Primary Examiner*—Thanh K Truong
(74) *Attorney, Agent, or Firm*—Buchanan Ingersoll & Rooney PC

(57) ABSTRACT

There is described a method of producing a sealed package of a pourable food product from a substantially tubular precut blank of sheet packaging material with opposite open ends. The method includes the steps of feeding the blank onto a relative forming mandrel; sealing one end of the blank to form a container open at the opposite end; removing the container from the mandrel; and sterilizing the container before filling it with the pourable food product; and the method also including the step of preheating the container by heating the mandrel before sterilizing the container.

8 Claims, 2 Drawing Sheets

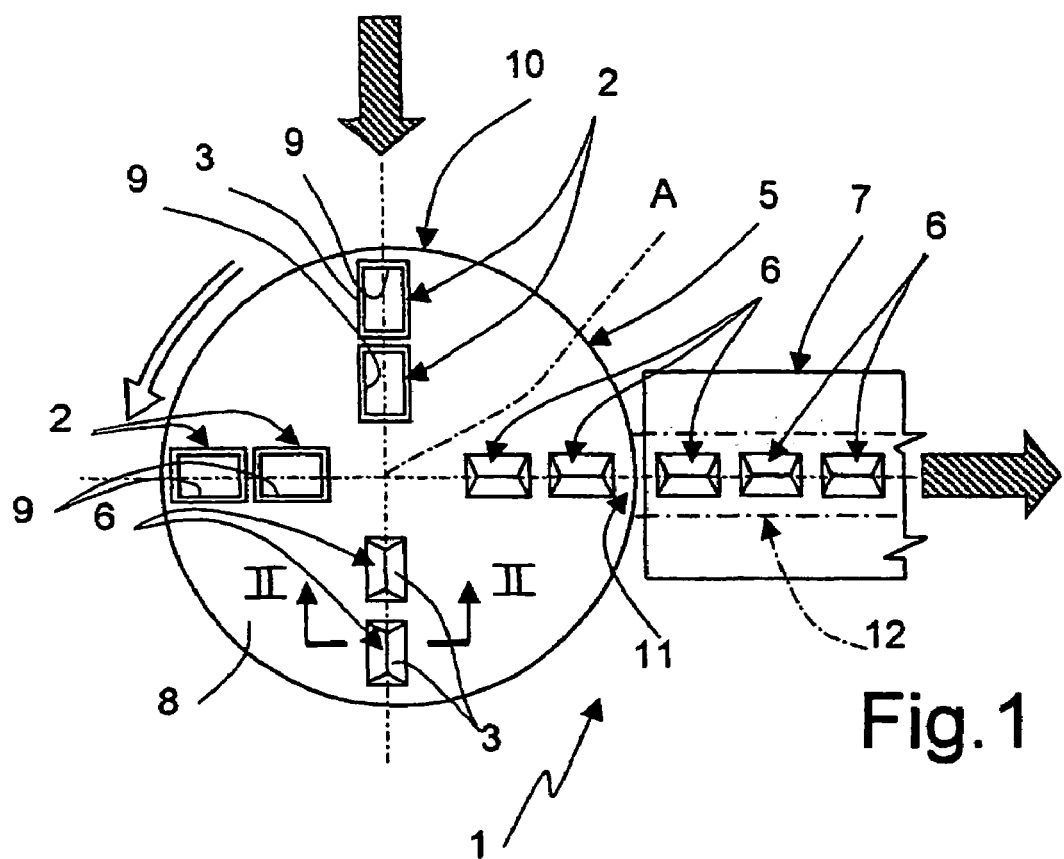
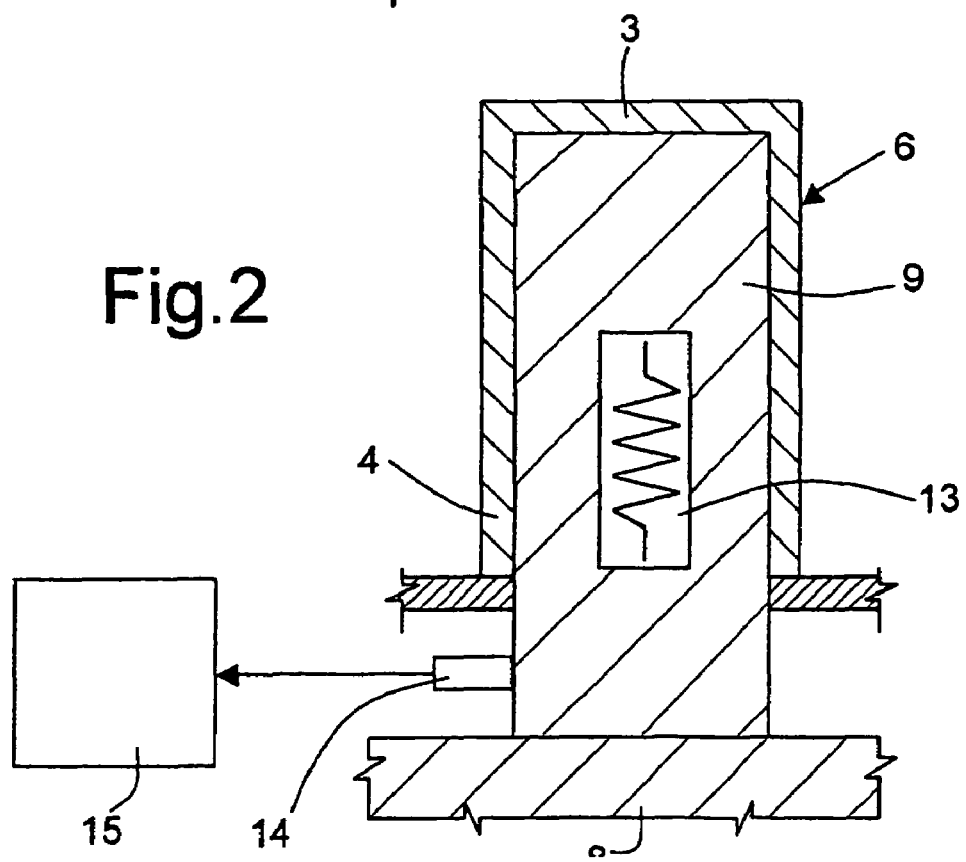

METHOD AND PACKAGING MACHINE FOR PRODUCING SEALED PACKAGES OF POURABLE FOOD PRODUCTS FROM PRECUT BLANKS OF SHEET PACKAGING MATERIAL

TECHNICAL FIELD

The present invention relates to a method and packaging machine for producing sealed packages of pourable food products from precut blanks of sheet packaging material.

BACKGROUND ART

As is known, many pourable food products, such as fruit juice, UHT (ultra-high-temperature treated) milk, wine, tomato sauce, etc., are sold in packages produced on fully automatic packaging machines from a succession of sheets of packaging material, which are folded to superimpose and seal the opposite edges, and so form respective substantially tubular or sleeve-shaped blanks open at both ends.

The packaging material may comprise a single- or multilayer plastic material, a polymer material, a mineral-filled polymer material, or a laminated cardboard-type material.

For example, one known cardboard-type packaging material has a multilayer structure comprising a layer of paper material covered on both sides with layers of heat-seal plastic material, e.g. polyethylene, and, in the case of aseptic packages for long-storage products, such as UHT milk, comprises a layer of barrier material defined, for example, by aluminium film, and which is superimposed on a layer of heat-seal plastic material and in turn covered with another layer of heat-seal plastic material eventually forming the inner face of the package contacting the food product.

To produce sealed packages on conventional packaging machines, the tubular blanks are fed onto respective forming mandrels movable along a given path. More specifically, the blanks are fed successively onto the respective forming mandrels at an input section; are each folded and sealed at one end along said path; and are removed from the mandrels at an output section, where they are fed onto a conveyor and transferred to an aseptic part of the packaging machine, where each is sterilized and filled. As is known, the axis of each forming mandrel may be horizontal and parallel to, or crosswise or vertical with respect to, its traveling direction.

More specifically, the folded ends of the blanks are normally sealed by pressing the ends between the respective ends of the forming mandrels and a heated pressure member, to obtain a number of containers, each with one open end through which to fill the container with the food product.

The sealed end may equally define the top or bottom of the finished package.

The open containers are fed by the relative conveyor into the aseptic part of the packaging machine and beneath a sterile-hot-air preheating station. Preheating normally lasts two machine cycles, and the sterile air is drawn from a tank and heated by electric resistance heaters.

The preheated containers are then fed to a sterilizing station where they are injected with a sterilizing agent in the form of vapour, normally with a hydrogen peroxide (H2O2) base, which is removed at a follow-up drying station.

The purpose of the preheating operation is to ensure the surface temperature of the containers at the sterilizing station is a few degrees higher than the condensation temperature of the hydrogen peroxide vapour; any residual hydrogen peroxide condensate, in fact, is difficult to remove at the drying station, which is designed solely to remove the vapour, and may therefore remain in the packaged product.

The amount of residual sterilizing agent permitted in the packaged product is governed by strict regulations, the maximum amount being in the region of 0.5 parts per million.

Packaging machines of the above type are used widely and satisfactorily in a wide range of food industries, and performance of the sterilizing station in particular more than meets requirements governing sterility of the packages and the amount of residual sterilizing agent.

Within the industry, however, a need is felt for further improvement, particularly as regards elimination of residual sterilizing agent.

Sterile-hot-air preheating fails to ensure even temperature over the entire heated inner surface of the containers, so that the temperature of certain surface areas, e.g. the corner regions, may be below the hydrogen peroxide vapour condensation temperature, thus resulting in localized condensation of the vapour and the consequences described above.

DISCLOSURE OF INVENTION

It is an object of the present invention to provide a method and packaging machine for producing sealed packages of pourable food products from precut blanks of sheet packaging material, designed to provide a straightforward, effective, low-cost solution to the above drawback.

According to the present invention, there is provided a method of producing sealed packages of pourable food products from precut blanks of sheet packaging material.

According to the present invention, there is also provided a packaging machine for producing sealed packages of pourable food products from precut blanks of sheet packaging material.

BRIEF DESCRIPTION OF THE DRAWINGS

A preferred, non-limiting embodiment of the present invention will be described by way of example with reference to the accompanying drawings, in which:

FIG. 1 shows a schematic top plan view of a packaging machine, in accordance with the present invention, for producing sealed packages of pourable food products from precut blanks of sheet packaging material;

FIG. 2 shows a larger-scale section along line II-II in FIG. 1;

BEST MODE FOR CARRYING OUT THE INVENTION

Figure 4:
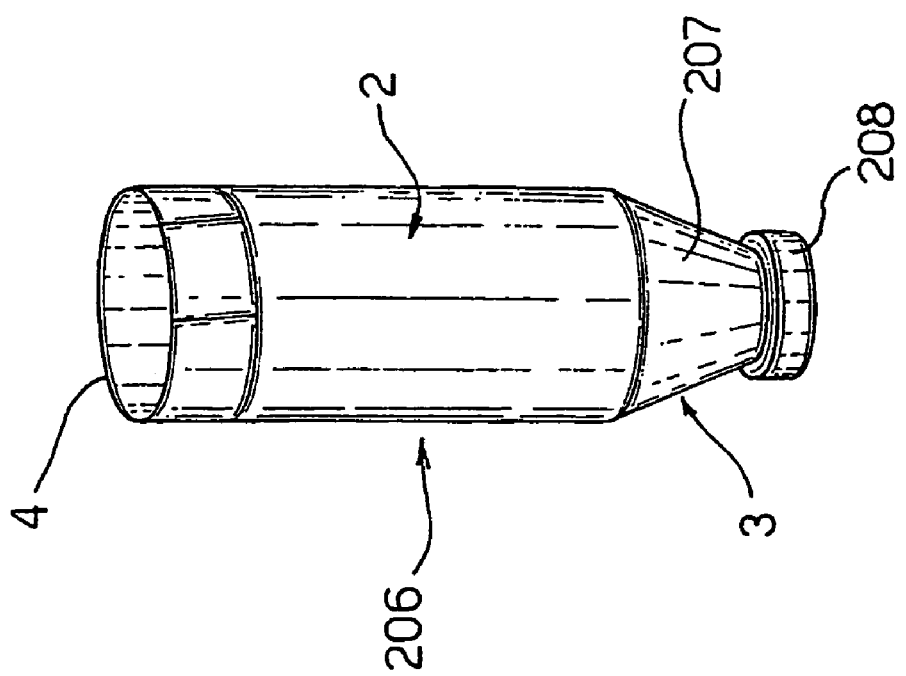
FIG. 4 is a perspective view of a semi-finished container having one end sealed with a neck portion provided with a screw cap, and one open end.

Number 1 in FIG. 1 indicates as a whole a packaging machine for producing sealed packages (not shown) of pourable food products from substantially tubular or sleeve-shaped precut blanks 2 of sheet packaging material with opposite open ends 3, 4 and circular or polygonal cross section.

As stated, the packaging material may comprise a laminated cardboard-type material, single- or multilayer plastic material, polymer material, or mineral-filled polymers.

Packaging machine 1 substantially comprises a sealing station 5 for sealing one (3) of ends 3, 4 of blanks 2 to form respective containers 6, open at the opposite end (4); and a sterilizing station 7 for sterilizing containers 6 before they are filled with the food product.

Figure 3:
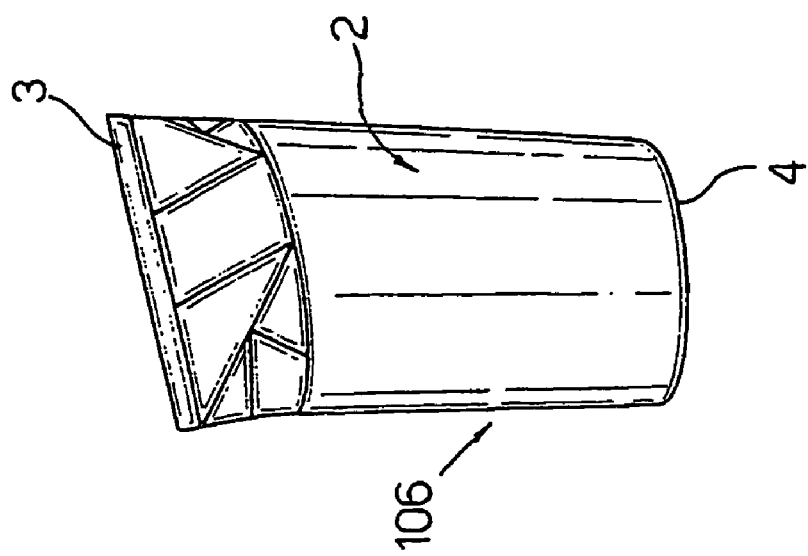
FIG. 3 is a perspective view of a semi-finished container having one sealed end and one open end.

More specifically, at sealing station 5, blanks 2 are fed along a path in the form of an arc of a circle with a vertical axis A, and are subjected—in known manner not described, by not being pertinent to the present invention—to successive operations to fold and seal ends 3. The sealed ends 3 may equally define the top or bottom of the finished packages. The ends 3 may be sealed by sealing together the inner surfaces of the tubular blank 2 to produce an open-ended semi-finished container 106 as shown in FIG. 3, or by sealingly connecting to the end 3 of the tubular blank 2 a neck portion 207, made e.g. of plastic material and provided with a closure 208 such as a screw cap and/or tearable membrane, to produce an open-ended semi-finished container 206 as shown in FIG. 4.

Blanks 2 are fed through sealing station 5 by a rotary member 8 of axis A, which has a number of peripheral forming mandrels 9 engaging respective blanks 2 and having respective longitudinal axes parallel to axis A.

Mandrels 9 are arranged in angularly equally spaced pairs; and the mandrels 9 in each pair are aligned in a radial direction with respect to axis A.

Alternatively, the longitudinal axes of mandrels 9 may be horizontal and parallel or crosswise to the feed direction.

Blanks 2 are fed successively onto respective mandrels 9 at an input section 10 of sealing station 5, and are removed from mandrels 9 at an output section 11 located, in the example shown, roughly 270° from input section 10 with reference to axis A. Mandrels 9 are detached from respective containers 6 by withdrawing mandrels 9 along their respective longitudinal axes.

At sterilizing station 7, containers 6 are fed by a conveyor 12 (shown schematically in FIG. 1) along a straight path, and are successively sterilized, by injection with a sterilizing agent in the form of vapour, e.g. hydrogen peroxide, and then dried to remove any residual sterilizing agent from containers 6.

To ensure the temperature of the inner surfaces of containers 6 at sterilizing station 7 is a few degrees higher than the hydrogen peroxide vapour condensation temperature, containers 6 are first preheated.

An important characteristic of the present invention lies in containers 6 being preheated by heating mandrels 9. For which purpose, any type of heating means can be used, e.g. a thermostatically controlled electric resistance heater 13, as shown in FIG. 2.

Each mandrel 9 is heated to a temperature ranging between ambient temperature and 95° C., and preferably between 50° C. and 95° C.

Each heater 13 is thermostatically controlled by a sensor 14 for detecting the temperature of relative mandrel 9, or any quantity related to it, and for supplying a corresponding temperature signal to a control unit 15 which controls heater 13 accordingly.

The packaging machine shown in FIGS. 1 and 2 is designed to produce parallelepiped-shaped containers 6; a packaging machine for forming substantially cylindrical containers 106, 206 will differ from packaging machine 1 only in being provided with substantially cylindrical mandrels.

The advantages of the present invention will be clear from the foregoing description.

In particular, by performing the preheating operation directly on mandrels 9 of rotary member 8, a dedicated station for preheating containers 6, 106, 206 upstream from sterilizing station 7 is no longer required, thus reducing the length of conveyor 12 and the total time taken to produce each package.

Moreover, heating mandrels provides for evenly heating the entire inner surface of containers 6, 106, 206, thus greatly reducing the risk of hydrogen peroxide vapour condensation when sterilizing containers 6, 106, 206, and so enabling the use of higher peroxide vapour concentrations with no risk of residual sterilizing agent remaining in the packaged product.

Finally, tests have shown that preheating containers 6, 106, 206 by heating mandrels calls for less energy than on known machines featuring a dedicated hot-air preheating station.

Clearly, changes may be made to packaging machine 1 and to the packaging method implemented thereby without, however, departing from the scope of the accompanying claims.

The invention claimed is:

1. A method of producing a sealed package of a pourable food product from a substantially tubular precut blank of sheet packaging material with opposite open ends, said method comprising:
   feeding said blank onto a forming mandrel;
   sealing one end of said blank on said mandrel to form a container open at the opposite end;
   removing said container from said mandrel;
   sterilizing said container before filling it with said pourable food product;
   preheating said container before sterilizing it, wherein the preheating of said container is performed by heating said mandrel;
   detecting a temperature of said mandrel; and
   controlling the preheating of said container by controlling the heating of said mandrel based on the detected temperature.

2. A packaging machine for producing sealed packages of pourable food products from substantially tubular precut blanks of sheet packaging material with opposite open ends, said machine comprising:
   a sealing station for sealing one end of said blanks to form respective containers open at the opposite end, and
   a sterilizing station for sterilizing said containers, said sealing station comprising a plurality of forming mandrels engaging respective blanks and traveling along a given path, along which each blank is converted into a container open at one end;
   wherein said sealing station comprises heating means for heating said mandrels to transmit heat to the containers before they are fed to said sterilizing station and means for controlling the temperature of each mandrel.

3. A machine as claimed in claim 2, wherein said heating means comprise an electric resistance heater for each mandrel.

4. A machine as claimed in claim 2, further comprising:
   a plurality of temperature sensors for detecting respective temperatures of the plurality of mandrels, wherein the controlling means controls each heating means based on the detected temperature to control the heating of each mandrel.

5. A machine as claimed in claim 2, further comprising:
   a sensor mounted on the mandrel for providing information relating to the temperature of the mandrel, wherein said means for controlling is operatively connected to the sensor to control the temperature of the mandrel based on information provided by the sensor.

6. A method of producing a sealed package of a pourable food product from a substantially tubular precut blank of sheet packaging material with opposite open ends, said method comprising:
   feeding said blank onto a forming mandrel;
   sealing one end of said blank on said mandrel to form a container open at the opposite end;

preheating said container by heating said mandrel to increase a temperature of an inner surface of the container;

removing said container from said mandrel; and sterilizing said container with hydrogen peroxide vapor at a sterilizing station, before filling the container with the pourable food product, the preheating of the container comprising preheating the container so that the temperature of the inner surface of the container at the sterilizing station is higher than a condensation temperature of the hydrogen peroxide vapor.

7. A packaging machine for producing sealed packages of pourable food products from substantially tubular precut blanks of sheet packaging material with opposite open ends, said machine comprising:

a sealing station for sealing one end of said blanks to form respective containers open at the opposite end, and a sterilizing station downstream of the sealing station for sterilizing said containers with a vapor sterilizing agent, said sealing station comprising a plurality of forming mandrels engaging respective blanks and traveling along a given path, along which each blank is converted into a container open at one end;

wherein said sealing station comprises heating means for heating said mandrels to transmit heat to an inner surface of each container so that the temperature of the inner surface of the container at the sterilizing station is higher than a condensation temperature of the vapor sterilizing agent.

8. A packaging machine as claimed in claim 7, further comprising a sensor mounted on one of the mandrels to provide information relating to the temperature of the one mandrel.

* * * * *